United States Patent [19]

Wojtkowski

[11] Patent Number: 4,960,957

[45] Date of Patent: Oct. 2, 1990

[54] PREPARATION OF PHENYLHYDROQUINONE

[75] Inventor: Paul W. Wojtkowski, Wilmington, Del.

[73] Assignee: E. I. Du Pont de Nemours and Company, Wilmington, Del.

[21] Appl. No.: 357,848

[22] Filed: May 30, 1989

[51] Int. Cl.$^5$ .................... C07C 37/00; C07C 39/12
[52] U.S. Cl. .................... 568/747; 568/744; 568/763
[58] Field of Search ............ 568/744, 747, 763, 767

[56] References Cited

U.S. PATENT DOCUMENTS 4,054,676  10/1977  Weinshenker et al. ............. 568/747
4,734,531  3/1988  Chang ............................... 568/744

FOREIGN PATENT DOCUMENTS 667229  7/1963  Canada ............................... 568/767
0140035  8/1983  Japan ................................. 568/744

OTHER PUBLICATIONS

J. F. Norris et al., Am. Chem. J., 29, 120 (1903).
G. B. Marini-Bettolo et al., Gazz. Chim. Ital., 80, 76 (1950).
J. Dobas, Chemicke listy, 46, 277 (1952).

Primary Examiner—Werren B. Lone

[57] ABSTRACT

A process for the preparation of phenylhydroquinone by the reaction of a mixture of a benzenediazonium salt, hydroquinone and water while maintaining the pH in the range of about 3 to about 9.

7 Claims, No Drawings

PREPARATION OF PHENYLHYDROQUINONE

FIELD OF THE INVENTION

This invention relates to the preparation of phenylhydroquinone by the reaction of hydroquinone with a benzenediazonium salt.

BACKGROUND OF THE INVENTION

Phenylhydroquinone is useful as a monomer in the preparation of polyesters which can be melt spun and subsequently processed into high strength/high modulus fibers, or into polyester molding granules for use in injection molding machines.

The preparation of phenylhydroquinone by the reaction of a benzenediazonium salts with hydroquinone is disclosed by J. F. Norris et al. in Am. Chem. J., 29, 120 (1903). However, the major product is said to be the ether, p-phenoxyhenol.

SUMMARY OF THE INVENTION

The present invention is a process for the preparation of phenylhydroquinone by the reaction of-a mixture containing water, a benzenediazonium and hydroquinone, while maintaining the pH of the mixture between about 3 and about 9, preferably about 5 to about 7.

Preferably the mixture also contains a water-immiscible solvent for phenylhydroquinone which is not a good solvent for hydroquinone, and the mixture is vigorously mixed to form a two phase mixture. The phenylhydroquinone, as it is formed, dissolves in the solvent.

Phenylbenzoquinone is also produced, and it is also soluble in the immiscible solvent. Phenylbenzoquinone may be reduced to phenylhydroquinone in situ, for example, by the addition of a finely divided metallic reducing agent such as iron or zinc, or the phenylbenzoquinone may be reduced by catalytic hydrogenation of the solution of phenylhydroquinone and phenylbenzoquinone in the immiscible solvent using conventional hydrogenation catalysts such as palladium.

DETAILED DESCRIPTION OF THE INVENTION

The reaction of a benzenediazonium salt and hydroquinone to produce phenylhydroquinone may be conducted at temperatures in the range of about 0° to about 200° C., preferably about 15° to about 95° C., and at pressures of about 0.5 atmospheres to about 2 atmospheres. The reaction of the benzenediazonium salt and hydroquinone will produce as a by-product diphenylhydroquinone in large amounts unless steps are taken to control this undesired reaction. The amount of this by-product can be controlled by having excess hydroquinone present in the reactor and also by removing phenylhydroquinone from the reaction phase promptly after it is formed. This latter step is accomplished in the preferred embodiment of present process by having a two-phase system, a water phase, in which the reaction of benzenediazonium salt and hydroquinone takes place, and a water-immiscible solvent phase for the phenylhydroquinone that is formed. The solvent should be a good solvent for phenylhydroquinone, and a poor or non-solvent for hydroquinone.

Suitable water-immiscible solvents for the phenylhydroquinone include halogenated hydrocarbons such as, methylene chloride; 1,1,2-trichloroethane; 1,1,1-trichloroethane; chlorobenzene and ortho-dichlorobenzene. Brominated fluorinated and mixed halogen hydrocarbon compounds such as chlorofluorocarbons are also believed suitable.

The pH of the reaction mixture should be maintained in the range of about 3 to about 9, preferably about 5 to about 7. This may be achieved by the periodic or continuous addition of suitable bases such as ammonium hydroxide, sodium hydroxide, sodium tetraborate, sodium hydrogen phosphate, and sodium acetate.

The benzenediazonium salt is normally slowly added to the other components in the mixture, and the pH maintained in the desired range by the slow addition of base.

Suitable benzenediazonium salts for the reaction with hydroquinone include benzenediazonium hydrogen sulfate, and benzenediazonium chloride.

The mole ratio of hydroquinone to benzenediazonium salt in the reaction mixture is preferably about 2:1, but higher or lower ratios can be tolerated. The ratio of water-immiscible solvent to water in the reactor is not critical. Normally water should be present in amount considerably in excess of the amount of hydroquinone, but all of the hydroquinone does not need to be dissolved in the water when the reaction is begun. The amount of water-immiscible solvent normally should be sufficient to dissolve the phenylhydroquinone produced.

The reduction of phenylbenzoquinone to phenylhydroquinone in the water-immiscible solvent may take place in situ, by the addition of finely divided metal. Or the reduction may take place by hydrogenating the chlorinated hydrocarbon solvent solution containing the phenylbenzoquinone and phenylhydroquinone. For example the hydrogenation can take place over a 1% palladium on carbon catalyst at 100° C. and 100 psig for a few minutes. Of course the crude mixture of reaction products could be separated from the immiscible solvent and then reduced, for example, by hydrogenation by dissolving the mixture in isopropyl alcohol and hydrogenating over a palladium on silica catalyst.

Preferably the reaction is carried out in an inert atmosphere, for example under nitrogen, because oxygen tends to convert the desired product into benzoquinones.

Example I (using a two phase system)

(A) Preparation of the diazonium salt

In a 250 ml Erlenmeyer flask with magnetic stirring is placed 9.31 gr (0.1 mole, 1 equivalent) of distilled aniline and 25 gr of ice. To this is added 19.6 gr (0.2 mole) of concentrated sulfuric acid. The mixture is cooled to 0–5° C. and 7.25 gr (0.105 mole) of sodium nitrite in 20 ml of water is added dropwise. This is stirred until solids are dissolved. Excess nitrous acid is destroyed by adding urea as demonstrated when a negative test is obtained with starch-iodide test paper. The clear yellow solution is made up to 65 ml by adding ice water thereby giving an ~1.5 M solution of benzenediazonium hydrogen sulfate.

(B) Reaction of benzenediazonium and hydroquinone

A 2-liter resin kettle is fitted with a Vibromixer® whose entry point is sealed from the atmosphere with a flexible rubber membrane, a $N_2$ inlet and outlet, a combination pH electrode, a dropping funnel, and a dropping funnel with glass jacket through which ice water is circulated via external pump. The cold benzene diazonium solution described above in (A) is placed in this dropping funnel.

Aqueous ammonium hydroxide (concentrated NH₄OH/H₂O ratio of 1 to 3) is placed in the other dropping funnel.

In the resin kettle is placed a solution of 22 gr of hydroquinone (0.20 mole, 2 eq.) in 280 ml of $N_2$-sparged water, 2.79 gr of iron dust (0.05 mole), and 800 ml of methylene chloride.

The mixture is stirred at room temperature so as to keep the aqueous layer completely mixed and the diazonium solution is added over ~30 min. while the pH is maintained at 5-7 by addition of the aqueous ammonium hydroxide. When addition is complete, the mixture is stirred for 1 hour at room temperature while maintaining the pH at 5-7.

The pH is lowered to 4 by addition of concentrated hydrochloric acid.

(C) Recovery of Product

Stopping the stirring results in the rapid separation of a clear dark red-brown methylene chloride layer and a cloudy orange aqueous layer which are subsequently separated from one another using a separating funnel. The aqueous layer is multiple extracted with a total of about 5 lb of ether. These extracts are dried over magnesium sulfate, filtered, and ether is removed under reduced pressure leaving 14.53 gr of a tan crystalline solid. The methylene chloride layer is dried over magnesium sulfate, filtered, and the methylene chloride is removed under reduced pressure leaving 13.19 gr of a soft dark brown solid.

(D) Analyses

Analysis of both solids by gas-liquid chromatography reveals a 65% yield of unreacted hydroquinone. This represents a recovery of 1.30 equivalents of the 2.0 equivalents used in the reaction. Analysis also reveals a yield of 0.52 equivalents of phenylhydroquinone which represents a 74% yield based on consumption of 0.70 equivalents of hydroquinone.

Example II (using an aqueous system)

Diazonium Preparation

In an Erlenmeyer flask in an ice bath with magnetic stirring is placed aniline (46.6 gr, 0.5 mole) and ice (125 gr). To this flask is added concentrated sulfuric acid (98 gr). The solution is cooled to about 5° C. and then slowly a solution of sodium nitrite (36.3 gr, 0.525 mole) in 100 ml water is added. When all solids dissolved, excess nitrous acid is destroyed with urea. The solution is treated with decolorizing carbon and then filtered.

Reaction

A 5-liter 4-necked Morton-flask is fitted with overhead stirrer, pH electrode, addition funnel containing concentrated ammonium hydroxide/water (1:3), a cooled jacketed addition funnel containing the above diazonium solution, and a nitrogen by-pass on one of the addition funnels. The flask is charged with 1800 ml water, hydroquinone (110 gr, 1.0 mole), iron dust (14 gr), and a few drops of concentrated sulfuric acid bringing the pH to approximately 7. The mixture is stirred and when the hydroquinone is in solution, the diazonium is added over approximately 2.25 hours while maintaining the pH at approximately 5-7 by addition of the aqueous ammonium hydroxide. When the addition is complete, the reaction mixture is stirred for one hour at room temperature. The pH is lowered to 4 by adding concentrated sulfuric acid. The reaction mixture is transferred to a separating funnel and layers are separated. The aqueous layer is extracted four times with one liter portions of methylene chloride and organic layers are combined. The combined organic layers are treated with decolorizing carbon, dried over magnesium sulfate, and filtered. Volatiles are removed on the rotary flash evaporator followed by a brief period on a vacuum pump leaving 64.4 gr of dark solid. The aqueous layers are extracted repeatedly with a total of twelve liters of ether. The ether extracts are dried over magnesium sulfate, filtered, and ether is removed on the rotary flash evaporator leaving 82.9 gr of tan solid. Analysis of both products by gas-liquid chromatography indicated a total of 38.1 gr of phenylhydroquinone and 78.6 gr of hydroquinone to be present.

I claim:

1. A process for the synthesis of phenylhydroquinone which comprises:

reacting at a temperature of about 0 degrees C to 200 degrees C, a mixture, containing water, a benzenediazonium salt and hydroquinone, while maintaining the pH of the mixture between about 3 and about 9.

2. The process of claim 1 in which the mixture also contains a water-immiscible solvent for phenylhydroquinone which is not a good solvent for hydroquinone, and in which the mixture is vigorously mixed to form a two phase mixture of water and the water-immiscible solvent, and in which the phenylhydroquinone is dissolved in the solvent at the end of the reaction.

3. The process of claim 2 in which the water-immiscible solvent is a halogenated hydrocarbon solvent.

4. The process of claim 3 in which the halogenated hydrocarbon solvent is selected from the class consisting of methylene chloride, 1,1,2-trichloroethane, 1,1,1-trichloroethane, chlorobenzene and o-dichlorobenzehe.

5. The process of claim 1 in which the benzenediazonium salt is selected from the class consisting of benzenediazonium hydrogen sulfate, and benzenediazonium chloride.

6. The process of claim 1 in which the pH is maintained by the addition of member selected from the class consisting of ammonium hydroxide, sodium hydroxide, sodium tetraborate, sodium hydrogen phosphate, and sodium acetate.

7. The process of claim 1 in which the amount of hydroquinone present is greater on a molar basis than the amount of benzenediazonium salt.

* * * * *